(12) United States Patent
Stankus et al.

(10) Patent No.: US 12,178,924 B2
(45) Date of Patent: Dec. 31, 2024

(54) MOBILE DISINFECTANT SYSTEM

(71) Applicants: Christopher J. Stankus, Southbury, CT (US); Robert D. Keeler, Stamford, CT (US)

(72) Inventors: Christopher J. Stankus, Southbury, CT (US); Robert D. Keeler, Stamford, CT (US)

( * ) Notice: Subject to any disclaimer, the term of this patent is extended or adjusted under 35 U.S.C. 154(b) by 564 days.

(21) Appl. No.: 15/931,268

(22) Filed: May 13, 2020

(65) Prior Publication Data
US 2021/0316020 A1    Oct. 14, 2021

Related U.S. Application Data

(60) Provisional application No. 63/009,732, filed on Apr. 14, 2020.

(51) Int. Cl.
*A61L 2/10*    (2006.01)

(52) U.S. Cl.
CPC .............. *A61L 2/10* (2013.01); *A61L 2202/11* (2013.01); *A61L 2202/122* (2013.01); *A61L 2202/14* (2013.01); *A61L 2202/15* (2013.01); *A61L 2202/16* (2013.01); *A61L 2202/20* (2013.01)

(58) Field of Classification Search
CPC .. A61L 2/10; A61L 2202/11; A61L 2202/122; A61L 2202/14; A61L 2202/15; A61L 2202/16; A61L 2202/20; A61L 2/24
See application file for complete search history.

(56) References Cited

U.S. PATENT DOCUMENTS

| | | | | |
|---|---|---|---|---|
| 2011/0079732 | A1* | 4/2011 | Kreitenberg | A61L 2/10 250/455.11 |
| 2012/0248332 | A1* | 10/2012 | Kreitenberg | A63B 47/04 250/455.11 |
| 2020/0205619 | A1* | 7/2020 | Gadde | A47K 3/281 |

* cited by examiner

*Primary Examiner* — Regina M Yoo
(74) *Attorney, Agent, or Firm* — ICE MILLER LLP (57) ABSTRACT

A mobile system for disinfecting a surface is described, having a chamber having an inner housing at least partially surrounding the surface, a disinfectant source at the inner housing to apply a disinfectant to at least one portion of the surface, and a motor for moving the chamber along a predetermined path from a first position to a second position, the at least one portion of the surface contacted by disinfectant changing as a result of the chamber moving from the first position to the second position.

14 Claims, 11 Drawing Sheets

MOBILE DISINFECTANT SYSTEM

CROSS-REFERENCE TO RELATED APPLICATIONS

This disclosure claims the benefit, under 35 U.S.C. § 119(e), of U.S. Provisional Patent Application No. 63/009,732, filed Apr. 14, 2020, the contents of which are incorporated herein by reference in their entirety.

TECHNICAL FIELD

The present teachings relate generally to systems and methods for disinfection and, more particularly, to mobile devices and methods for disinfection of surfaces.

BACKGROUND

It is known in the art that ultraviolet (UV) light can be used as a disinfectant. UV disinfection systems expose microorganisms to a lethal dose of UV energy that kills or inactivates microorganisms on surfaces. The UV dose is measured as the product of UV light intensity times the exposure time within the UV lamp array. UV light at the germicidal wavelength of about 253.7 nanometers (nm), alters the genetic (DNA) material in cells so that bacteria, viruses, molds, algae and other microorganisms are considered dead and can no longer reproduce. Thus, the risk of humans transmitting any disease from them is eliminated.

Common UV lamps include mercury-vapor lamps, and more recently, UVC LEDs or ultra-violet C light emitting diodes. These lamps can emit light between about 250 nm-280 nm to irradiate microorganisms on a surface.

Other common disinfectants include sprays and wipes with at least 70% alcohol. Unlike UV lamps, these disinfectants require replenishment of consumables.

It is important to disinfect commonly touched areas often to reduce the transmission of bacteria, viruses, etc. between humans. Such commonly touched areas include grab handles on public transportation vehicles (e.g. subways, trains, monorails, buses, and airplanes), handrails, and door handles. However, it is not possible to disinfect these commonly touched areas as often as required.

For example, cleaning with a disinfectant solution requires a person to clean the surface, but it is not economically feasible to station someone to clean the commonly touched areas 24-7. Current mechanical spray devices cannot precisely target the areas to be disinfected and creates harmful overspray to nearby people. UV light disinfectant hand wands also require a person to utilize the device and can be ineffective if the person moves the UV light too quickly over the surface before the microorganisms are killed or inactivated. UV lights mounted on robots do not precisely target the commonly touched areas and cannot be used while people are around as UV light is harmful to human eyes and skin. Thus, the space around the commonly touched area being disinfected needs to be isolated, or taken out of service (in the case of a mass transit vehicle).

For these reasons above, it is common that these commonly touched areas are only cleaned once per daily. This is not enough as the very first person to touch an area, e.g., a grab handle, after it was cleaned could infect the surface with a virus that is then transmitted to countless people in a 24-hour period.

Therefore, it would be beneficial to have a disinfectant system that automatically disinfects the surface of commonly touched areas throughout the day.

SUMMARY

The needs set forth herein as well as further and other needs and advantages are addressed by the present embodiments, which illustrate solutions and advantages described below.

In one aspect of the invention, a mobile system for ultraviolent (UV) disinfection is provided having a disinfectant chamber that at least partially covers a surface and has a first end and a second end, and an inner housing and outer housing, the disinfectant chamber having a drive motor to travel along the surface, a UV light source at the inner housing to disinfect the surface, and a sensor.

In another aspect, a mobile system for ultraviolent (UV) disinfection is provided having a disinfectant chamber that at least partially covers a surface and has a first end and a second end, and an inner housing and outer housing, the disinfectant chamber having a UV light source at the inner housing to disinfect the surface, and a sensor, and a link that moves the disinfectant chamber along the surface.

In another aspect of the invention, a system for controlling a disinfectant system is provided having a computer, a device in communication with the computer, a disinfectant system in communication with the computer, software executing on the computer for receiving credentials and a command from a device and sending at least a part of the command to the disinfectant system, and software executing on the computer for receiving a status of the disinfectant system.

In another aspect of the invention, a mobile system for disinfection is provided having a disinfectant chamber that at least partially covers a surface and has a first end and a second end, and an inner housing and outer housing, the disinfectant chamber having a drive motor to travel along the surface, a spray nozzle at the inner housing to spray disinfectant on the surface, and a sensor.

In another aspect of the invention, a mobile system for disinfection is provided having a disinfectant chamber that at least partially covers a surface and has a first end and a second end, and an inner housing and outer housing, the disinfectant chamber having a drive motor to travel along the surface, a disinfectant wipe at the inner housing to disinfect the surface, and a sensor.

In another aspect of the invention, a mobile system for disinfecting a surface is described, having a chamber having an inner housing at least partially surrounding the surface, a disinfectant source at the inner housing to apply a disinfectant to at least one portion of the surface, and a motor for moving the chamber along a predetermined path from a first position to a second position, the at least one portion of the surface contacted by disinfectant changing as a result of the chamber moving from the first position to the second position.

Other embodiments of the system and method are described in detail below and are also part of the present teachings.

For a better understanding of the present embodiments, together with other and further aspects thereof, reference is made to the accompanying drawings and detailed description, and its scope will be pointed out in the appended claims.

DETAILED DESCRIPTION

The present teachings are described more fully hereinafter with reference to the accompanying drawings, in which the present embodiments are shown. The following description is presented for illustrative purposes only and the present teachings should not be limited to these embodiments.

In compliance with the statute, the present teachings have been described in language more or less specific as to structural and mechanical features. It is to be understood, however, that the present teachings are not limited to the specific features shown and described, since the apparatus, systems, and methods herein disclosed comprise preferred forms of putting the present teachings into effect.

For purposes of explanation and not limitation, specific details are set forth such as particular structures, architectures, interfaces, techniques, etc. in order to provide a thorough understanding. In other instances, detailed descriptions of well-known devices and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first," "second," etc, for different features/components of the present disclosure are only intended to distinguish the features/components from other similar features/components and not to impart any order or hierarchy to the features/components.

To aid the Patent Office and any readers of any patent issued on this application in interpreting the claims appended hereto, Applicant does not intend any of the appended claims or claim elements to invoke 35 U.S.C. 112(f) unless the words "means for" or "step for" are explicitly used in the particular claim.

Figure 1:
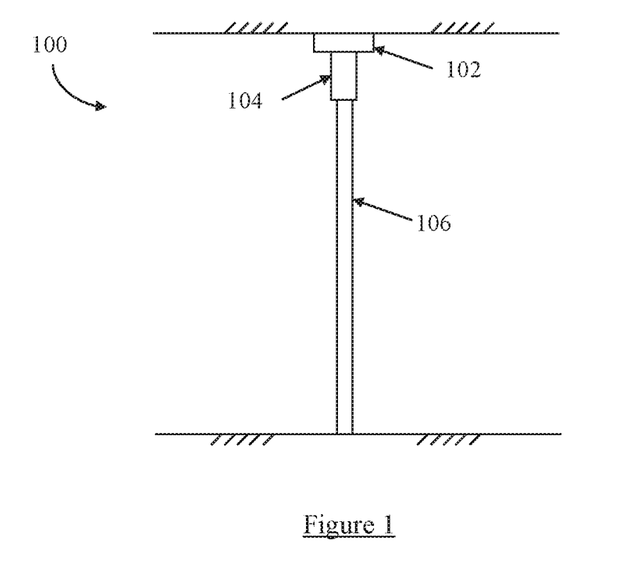
FIG. 1 is a diagram showing a disinfectant system according to the present teachings.

Referring now to FIG. 1, shown is a diagram of one embodiment of the disinfectant system 100 according to the present teachings. The disinfectant system 100 may include a disinfectant chamber 104 and an optional docking station 102, although not limited thereto. The disinfectant chamber 104 can have a transverse cross section of a circle to fully wrap around the surface 106 to be disinfected. The disinfectant chamber 104 can also have a transverse cross section that is approximately "U"-shaped or similar or any other shape, to at least partially cover a surface 106 to be disinfected, an example illustrated in FIG. 8. The disinfectant chamber 104 may also split longitudinally into two pieces to install on the surface 106, and then reconnect into one unit. The disinfectant chamber 104 may be shaped as a cylinder, and/or shaped to fit the surface 106.

The disinfectant chamber 104 may travel from the optional docking station 102 along surface 106 to disinfect it using UV lamps, disinfectant sprays, wipes, or other known methods (e.g., other types of light such as blue or red light), and then return back to the optional docking station 102. The surface 106 may include, but is not limited to, grab handles/poles, door handles, handrails, and other surfaces that may be commonly touched. In FIG. 1, surface 106 is depicted as a grab handle as an exemplary embodiment.

The optional docking station 102 may provide resources to the disinfectant chamber 104. For example, the optional docking station 102 may charge a battery in the disinfectant chamber 104, and may also provide power to and/or mechanically move the disinfectant chamber 104 along the surface 106. The optional docking station 102 may also refill any liquid, gas, or aerosol disinfectant. The optional docking station 102 may have a processor and/or data storage to communicate with the disinfectant chamber 104, communicate with other disinfectant systems 100s, and communicate with a server or other devices, e.g., computers or smart phones. Communicated data may include, but is not limited to, commands (e.g., activate or schedule activation of the disinfectant chamber 104), device status (e.g., error messages from the docking station 102 or disinfectant chamber 104, or the level of consumables), diagnosis, and record disinfections.

The disinfectant chamber 104 may be stored at the optional docking station 102, which may be located on either end of the surface 106.

Figure 2:
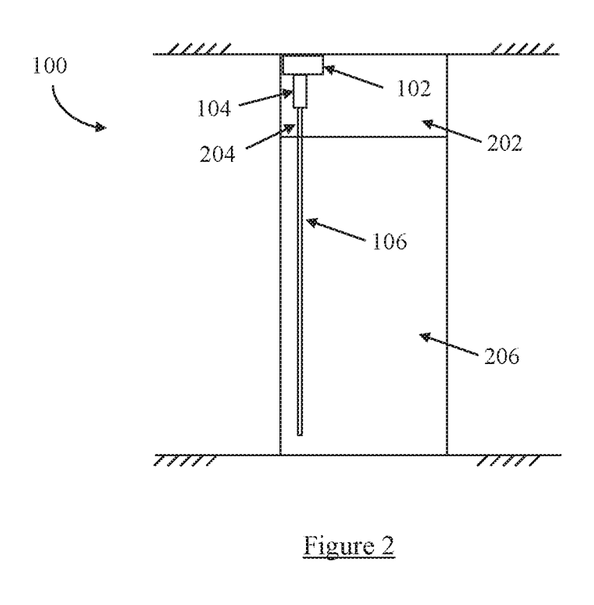
FIG. 2 is a diagram showing a disinfectant system according to the present teachings.

Referring now to FIG. 2, shown is a diagram of one embodiment of the disinfectant system 100 according to the present teachings. In FIG. 2, surface 106 is depicted as a door handle as an exemplary embodiment, which is mounted on door 206. The disinfectant chamber 104 may travel from the optional docking station 102 along guide pole 204 onto the surface 106 to disinfect it using UV lamps, disinfectant sprays, wipes, or other known methods (e.g., other types of light such as blue or red light), and then return back to the optional docking station 102. The disinfectant chamber 104 may be stored at the optional docking station 102, which may be located on the wall 202 above the door or above the ceiling.

Figure 3:
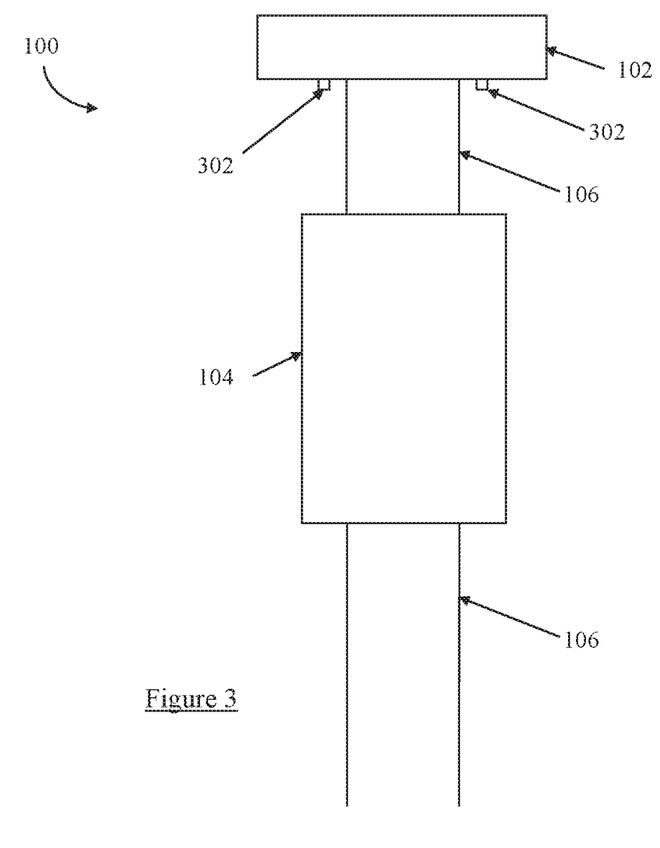
FIG. 3 is a diagram showing a disinfectant system according to the present teachings.

Referring now to FIG. 3, shown is a diagram of one embodiment of the disinfectant system 100 according to the present teachings. Optional docking station 102 may include docking pin 302, which may electrically connect to the disinfectant chamber 104. For example, the optional docking station may charge a battery in the disinfectant chamber 104 and/or communicate data to/from the docking station, as described herein, through the docking pin 302.

Figure 4:
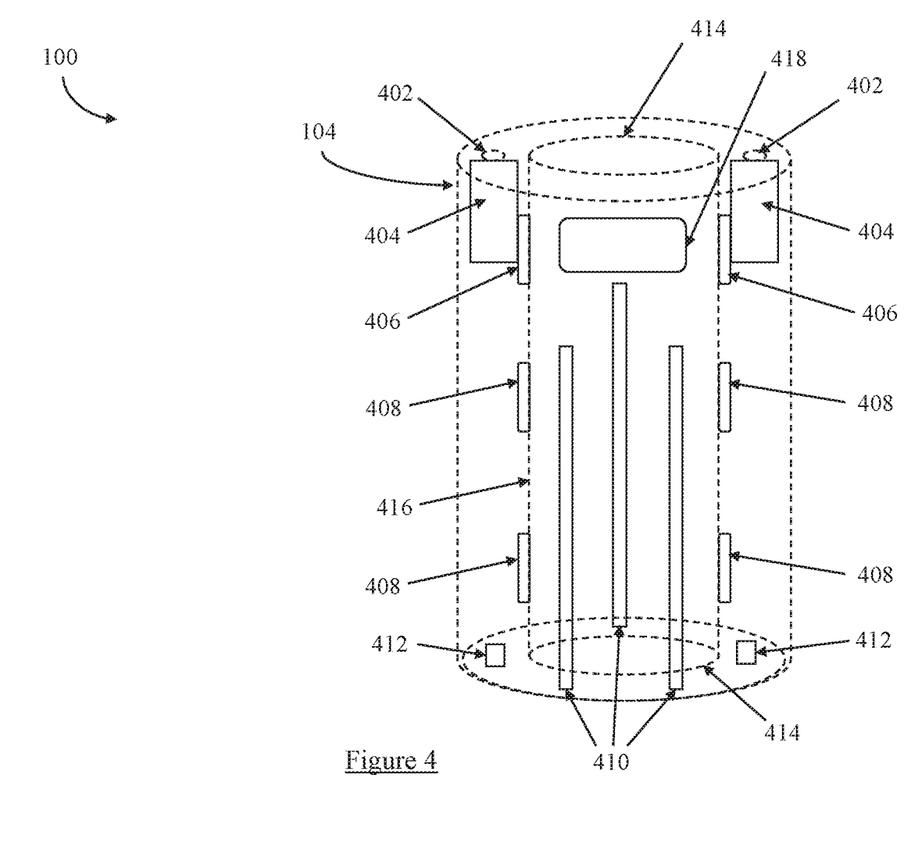
FIG. 4 is a diagram showing a disinfectant system according to the present teachings.

Referring now to FIG. 4, shown is a diagram showing one embodiment of the disinfectant system 100 according to the present teachings. The disinfectant system 100 may include a disinfectant chamber 104 that has a chamber pin 402, power box 404, drive wheel 406, guide wheel 408, UV lamp 410, sensor 412, gasket 414, and inner wall 416.

The chamber pin 402 may electrically connect to the optional docking station 102 to charge a battery in the disinfectant chamber 104 and/or communicate data to/from the docking station, as described herein. The chamber pin 402 may connect to the power box 404.

The power box 404 may contain a processor and/or data storage, a drive motor, and/or a battery. The processor may control the disinfectant chamber 104, including the drive motor. The processor may communicate with the optional docking station 102 through the chamber pin 402, or wirelessly. The processor may also control the drive motor, UV lamp 410, store data, communicate with other disinfectant systems 100s, and communicate with a server or other devices, e.g., computers or smart phones. Communicated data may include, but is not limited to, commands (e.g., activate or schedule activation of the disinfectant chamber 104), device status (e.g., error messages from the docking station 102 or disinfectant chamber 104), diagnosis, and record disinfections.

The drive motor in the power box 404 may connect to a drive wheel 406 to enable the disinfectant chamber 104 to travel along the surface 106. One or more drive wheels 406 may compress against the surface 106 to enable the disinfectant chamber 104 to travel along the surface 106. The drive wheel 406 may also compress against the surface 106 with one or more guide wheels 408 to enable the disinfectant chamber 104 to travel along the surface 106. One or more guide wheels 408 may also compress against the surface 106 to enable the disinfectant chamber 104 to travel along the surface 106 and to keep the disinfectant chamber 104 centered on the surface so that inner wall 416 does not touch the surface 106.

The battery in the power box 404 may provide power to the disinfectant chamber 104, including the UV lamp 410, sensor 412, processor, and drive motor. The battery may be charged by the optional docking station 102 through the chamber pin 402, or wirelessly. The battery may be an alkaline battery, e.g., 9B, N, J, D, C, AA, AAA, etc. The battery may be a lithium ion battery or other type of rechargeable battery.

The UV lamp 410 is located at the inner wall 416 of the disinfectant chamber 104 and can emit light to irradiate microorganisms on a surface. The amount (strength and time) of light to kill or inactivate microorganisms is known in the art. Inner wall 416 may be made of a reflective material to reflect light bouncing off the surface 106 back onto the surface 106. Inner wall 416 may be cylindrical as shown in FIG. 4, or may be any other shape to correspond to the surface 106.

As UV light can be harmful to humans, the gasket 414 may be located between the outer edge of the disinfectant chamber 104 and the surface 106. The gasket 414 may block or screen nearby humans from harmful UV light that may emit from the disinfectant chamber 104. For example, if the disinfectant chamber 104 has a transverse cross section of a circle, the gasket 414 may be located at each end of the disinfectant chamber 104. If the disinfectant chamber 104 has a transverse cross section that is approximately "U"-shaped or similar or any other shape, the gasket 414 may be located at each end and along the side of the disinfectant chamber 104, an example illustrated in FIG. 8.

The sensor 412 may be located at one or both ends of the disinfectant chamber 104. The sensor 412 may be a touch and/or vision sensor to detect the end of the surface 106 or detect an obstruction on the surface 106.

It is appreciated that UV lamp 410 may be replaced with one or more containers 418 having disinfectant and a spray nozzle to spray disinfect on the surface. The container may include one or more reservoirs 418 for storing liquid, gas, or aerosol disinfectant.

It is also appreciated that UV lamp 410 may be replaced with a disinfectant wipe to disinfect the surface.

Figure 5:
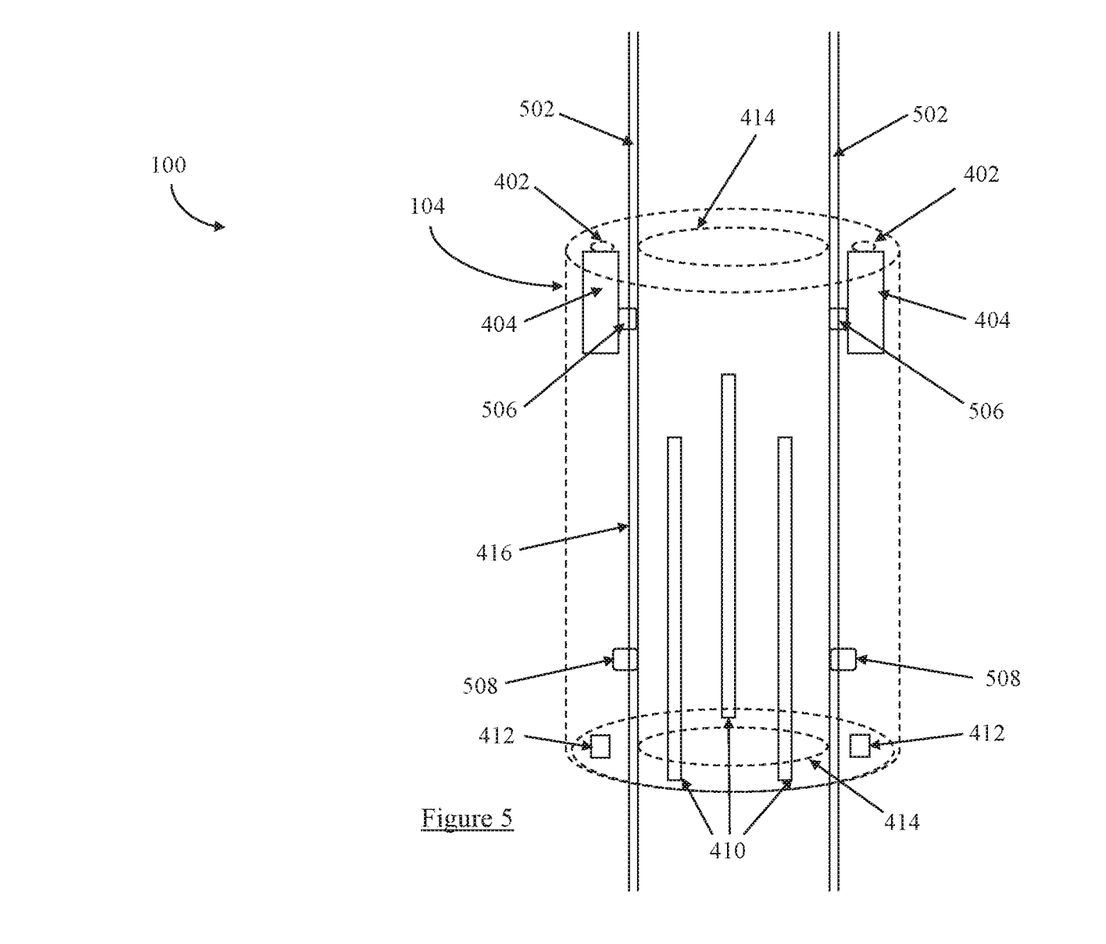
FIG. 5 is a diagram showing a disinfectant system according to the present teachings.

Referring now to FIG. 5, shown is a diagram showing one embodiment of the disinfectant system 100 according to the present teachings. The disinfectant system 100 may include a track 502 and a disinfectant chamber 104 that has a chamber pin 402, power box 404, track drive 506, track guide 508, UV lamp 410, sensor 412, gasket 414, and inner wall 416.

One or more tracks 502 may be connected to the surface 106. The disinfectant chamber 104 may travel along the track 502. The drive motor in the power box 404 may connect to a track drive 506, which connects to the track 502 to enable the disinfectant chamber 104 to travel along the surface 106. One or more track guides 508 may also connect to the track 502 to enable the disinfectant chamber 104 to travel along the surface 106 and to keep the disinfectant chamber 104 centered on the surface so that inner wall 416 does not touch the surface 106.

Figure 6:
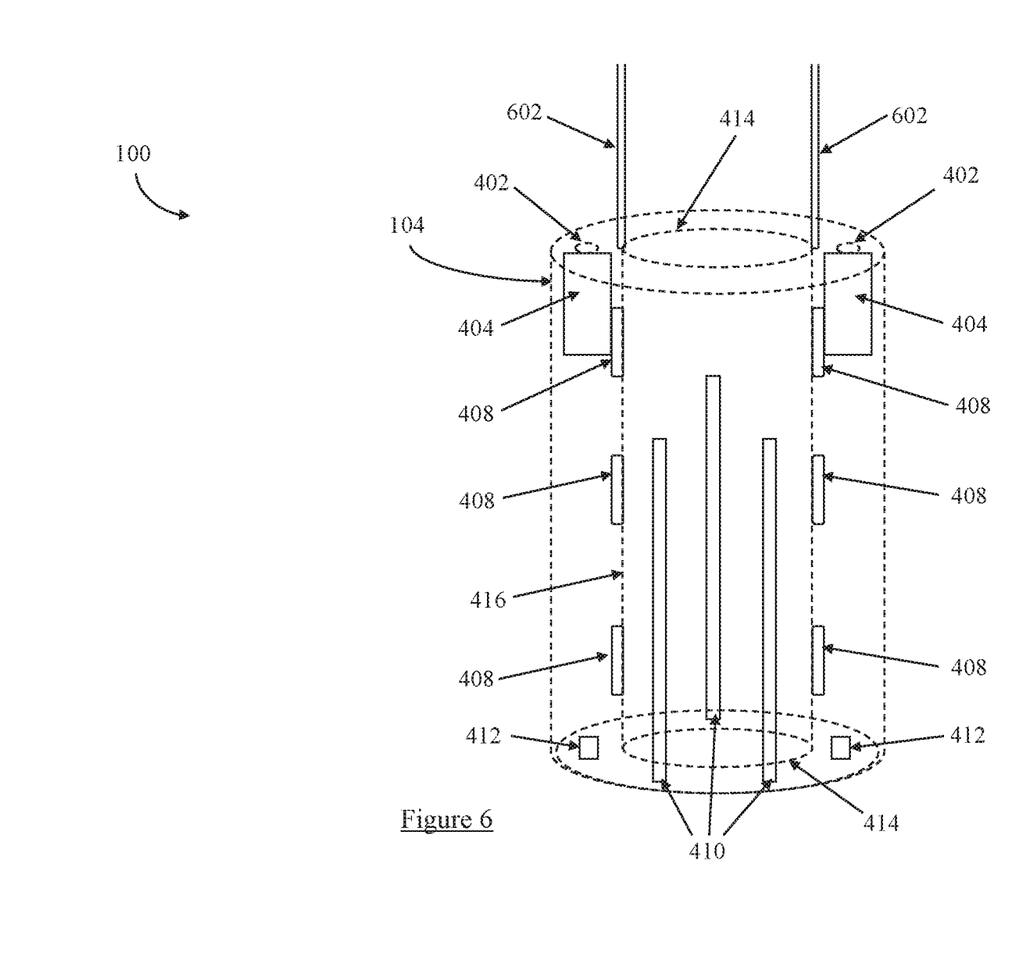
FIG. 6 is a diagram showing a disinfectant system according to the present teachings.

Referring now to FIG. 6, shown is a diagram showing one embodiment of the disinfectant system 100 according to the present teachings. The disinfectant system 100 may include a link 602 and a disinfectant chamber 104 that has a chamber pin 402, power box 404, guide wheel 408, UV lamp 410, sensor 412, gasket 414, and inner wall 416.

One or more links 602 may be connected to one end of the disinfectant chamber 104. The link 602 may include, but is not limited to, a cable or rod to move the disinfectant chamber 104 along the surface 106, a power cable to power the disinfectant chamber 104, a light guide to provide UV light to the disinfectant chamber 104, a tube to provide liquid, gas, or aerosol disinfectant to a reservoir, and/or a communication cable to communicate data to/from the disinfectant chamber 104. In situations where a light guide is used, the UV lamp 410 may be remote from the disinfectant chamber 104.

In an embodiment, a winch system (not shown) moves the disinfectant chamber 104 along the surface 106 via the link 602.

In an embodiment, a winch and brake system (not shown) moves the disinfectant chamber 104 along the surface 106 via the link 602.

In an embodiment, a pulley system (not shown) moves the disinfectant chamber 104 along the surface 106 via the link 602.

In an embodiment, a push/pull rod system (not shown) moves the disinfectant chamber 104 along the surface 106 via the link 602.

In an embodiment, the disinfectant chamber 104 contains a winch and brake system or a push/pull rod system to move the disinfectant chamber 104 along the surface 106 via the link 602.

In an embodiment, the link 602 is connected between the disinfectant chamber 104 and the docking station 102. The docking station 102 contains a winch and brake system or a push/pull rod system to move the disinfectant chamber 104 along the surface 106 via the link 602.

Figure 7:
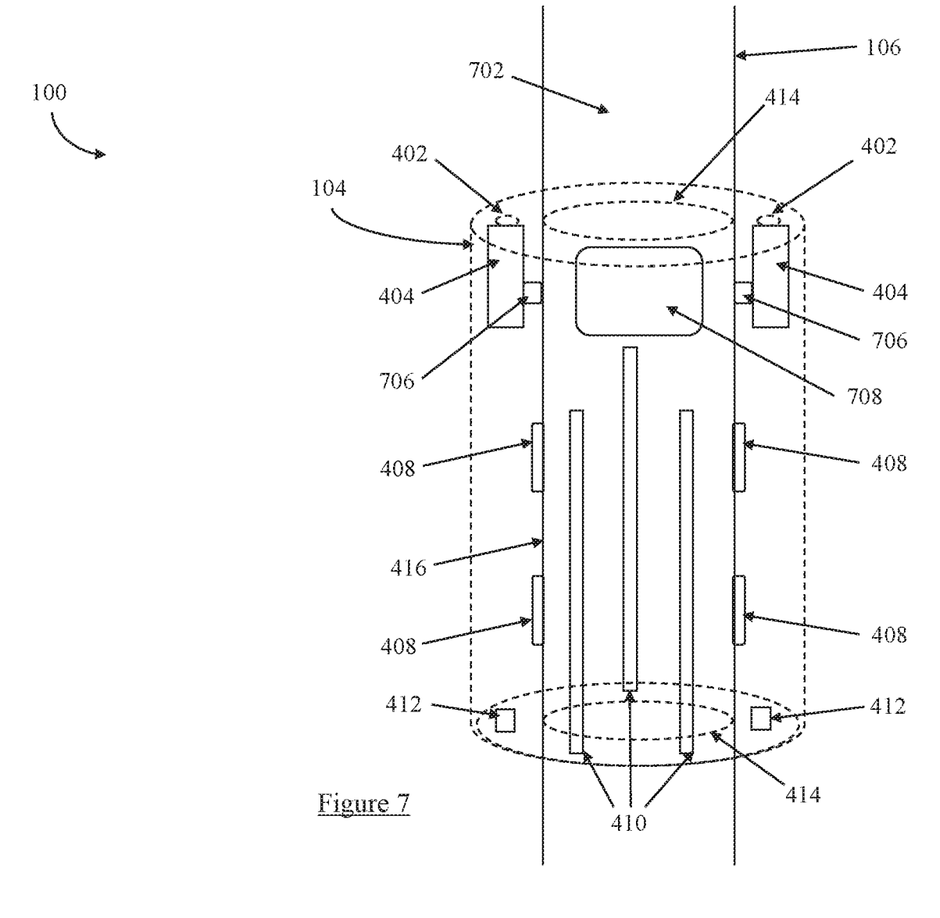
FIG. 7 is a diagram showing a disinfectant system according to the present teachings.

Referring now to FIG. 7, shown is a diagram showing one embodiment of the disinfectant system 100 according to the present teachings. The disinfectant system 100 may include a solenoid 702 (not shown), a magnet 708, and a disinfectant chamber 104 that has a solenoid drive 706, chamber pin 402, power box 404, guide wheel 408, UV lamp 410, sensor 412, gasket 414, and inner wall 416.

A solenoid 702 may be under the surface 106, which moves the magnet 708 under the surface 106. The solenoid drive 706 magnetically connects to the magnet 708 to enable the disinfectant chamber 104 to travel along the surface 106.

Figure 8:
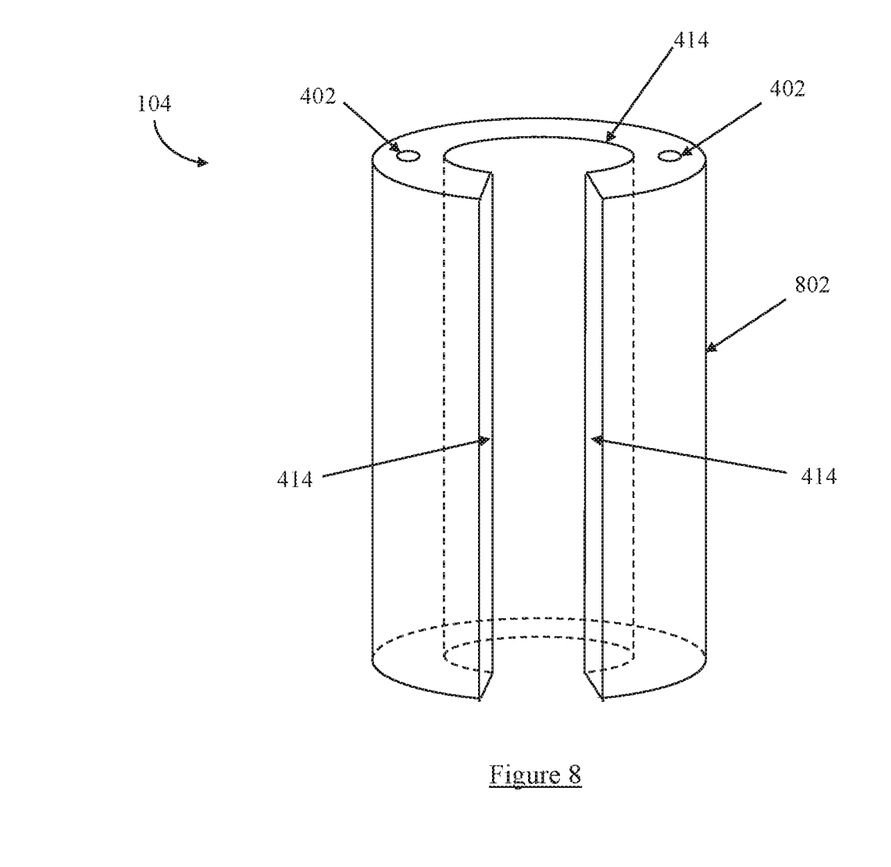
FIG. 8 is a diagram showing a disinfectant chamber according to the present teachings.

Referring now to FIG. 8, shown is a diagram showing one embodiment of the disinfectant chamber 104 according to the present teachings. The disinfectant chamber 104 may include a chamber pin 402, gasket 414, and outer housing 802.

The disinfectant chamber 104 can also have a transverse cross section that is approximately "U"-shaped or similar or any other shape, to at least partially cover a surface 106 to be disinfected. The gasket 414 may be located between the outer edge of the disinfectant chamber 104 and the surface 106. For example, the gasket 414 may be located at each end and along the side of the disinfectant chamber 104.

Figure 9:
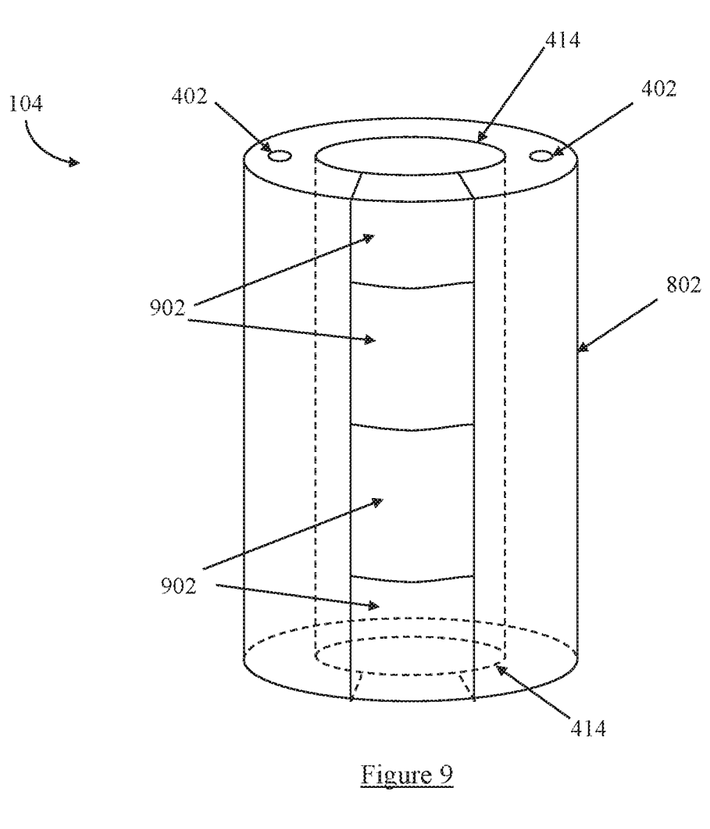
FIG. 9 is a diagram showing a disinfectant chamber according to the present teachings.

Referring now to FIG. 9, shown is a diagram showing one embodiment of the disinfectant chamber 104 according to the present teachings. The disinfectant chamber 104 may include a chamber pin 402, gasket 414, outer housing 802, and door 902.

One or more door 902 may be located on the outer housing 802. The outer housing 802 may be cylindrical as shown in FIG. 8, or may be any other shape. The door 902 may open when the disinfectant chamber 104 senses (e.g., via the sensor 412) a permanent obstruction on the surface 106. For example, a permanent obstruction may be a mounting bracket that anchors a door handle or handrail, or a baluster or spindle connected to a handrail. The door 902 opens to allow the disinfectant chamber 104 to pass-by the support member, and then closes once the disinfectant chamber 104 is past the obstruction.

Figure 10:
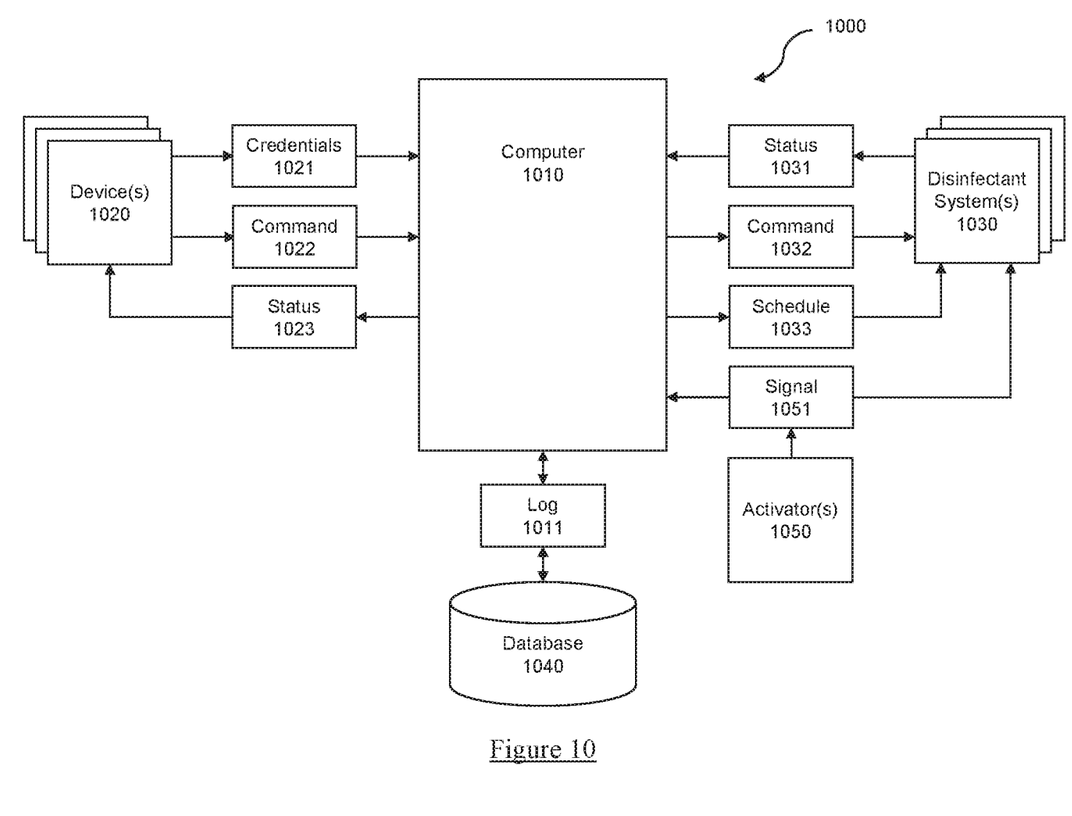
FIG. 10 is a diagram showing a control system for the disinfectant system according to the present teachings.

Referring now to FIG. 10, a control system 1000 usable with the disinfectant system is disclosed.

The control system 1000 includes a computer 1010. The computer 1010 may be a processor, remote computer, computer server, network, mobile device, smartphone or any other computing resource.

The computer 1010 may be in communication with devices 1020. Devices 1020 may be a computer, laptop, smartphone, tablet, or other electronic device capable of transmitting data to the computer 1010. Device 1020 may have an application configured to communicate with computer 1010.

The computer 1010 may be in communication with one or more disinfectant systems 1030, such as the disinfectant system 100 previously described. The disinfectant systems 1030 may be in wired or wireless communication with the computer 1010.

Devices 1020 may also be in communication with disinfectant systems 1030, either through computer 1010 or directly. Direct communication with disinfectant systems 1030 may take place via WIFI, Bluetooth, USB, or other known methods.

The computer 1010 may also be in communication with a database 1040. The database 1040 may store information regarding the system 1000. The database 1040 may be a storage drive or array accessible to computer 1010, or cloud storage.

The computer 1010 may also be in communication with an activator 1050. The activator 1050 may be a switch, a button, a sensor, or a timer. The activator 1050 may, for example, be a touch sensor, that determines when the surface 106 is touched. When the surface 106 is no longer being touched, activator 1050 may actuate the disinfectant system 1030 associated with the surface 106.

Multiple devices 1020 may be in communication with each other, and may pass communications from one device to other devices 1020, the computer 1010, or disinfectant systems 1030. Disinfectant systems 1030 may also be in communication with each other, and may pass communications from one disinfectant system 1030 to other disinfectant systems 1030, the computer 1010, or devices 1020.

The computer may receive credentials 1021 from devices 1020, which it may check to determine whether the device is authorized to access the system 1000.

The computer 1010 may receive a command 1022 from the device 1020. The command 1022 may request a status of the disinfectant systems 1030, direct the disinfectant systems to actuate, or set a schedule for the disinfectant systems 1030, among other things. The command 1022 may be directed to all or some of the disinfectant systems 1030. The computer 1010 may forward the command 1022 to the disinfectant system as command 1032.

The computer 1031 may receive a status from the disinfectant systems 1030, either automatically or in response to a command from the device 1020 or generated by the computer 1010. The status may indicate whether the disinfectant system is currently activated, the last time it was activated, the next time it will activate, the levels of any consumables, any faults, or any other status information. The computer 1010 may forward the status 1031 to the device 1020 as status 1023.

The computer may also provide a schedule 1033 to the disinfectant systems 1030. The schedule 1033 may be based on a command 1022, or may be generated by the computer. The schedule may actuate the disinfectant system 1030 at predetermined times, or at predetermined times after an event happens.

Activators 1050 may also be in communication with disinfectant system 1030. Activators 1050 may send a signal to the computer 1010, or the disinfectant systems 1030, either individually or as a group. The signal 1030 may command the disinfectant system 1030 to clean.

The computer 1010 may store any of the credentials 1021, commands 1022, 1032, statuses 1031, 1023, schedule 1033, and/or signal 1051, along with any other relevant data, such as part numbers and serial numbers of devices 1020 or disinfectant systems 1030, etc., in a log 1011. The log 1011 may be provided to and retrieved from the database 1040.

Figure 11:
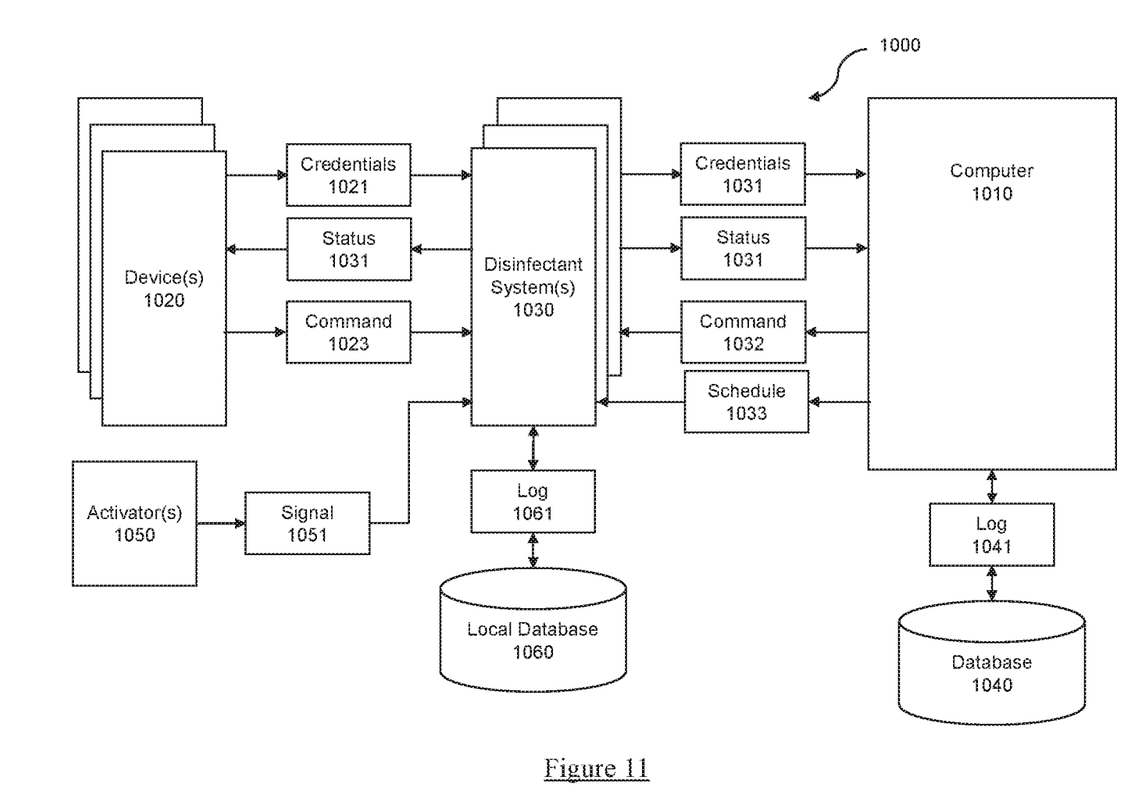
FIG. 11 is a diagram showing a control system for the disinfectant system according to the present teachings.

As shown in FIG. 11, the system 1000 may be configured such that the devices 1020 communicate directly with the disinfectant systems 1030, which act as a cutoff or an intermediary between the devices 1020 and the computer 1010.

Notably, FIG. 11 also includes local database 1060, where disinfectant systems 1030 may store and retrieve logs 1061. Logs 1061 may include the same types of information logs 1041. There may be a single local database 1060 for all disinfectant systems 1030, or there may be multiple local databases 1060, for example, for groups of or single disinfectant systems 1030.

While the present teachings have been described above in terms of specific embodiments, it is to be understood that they are not limited to these disclosed embodiments. Many modifications and other embodiments will come to mind to those skilled in the art to which this pertains, and which are intended to be and are covered by this disclosure. It is intended that the scope of the present teachings should be determined by proper interpretation and construction of this disclosure and its legal equivalents, as understood by those of skill in the art relying upon the specification and the attached drawings.

What is claimed is:

1. A system for disinfecting, comprising:
a door having a door handle with a surface to be disinfected;
a chamber having an inner housing, the chamber at least partially surrounding the surface of the door handle;
an ultraviolet light source located at the inner housing to apply ultraviolet light on at least one portion of the surface of the door handle; and
a motor located on the chamber for moving the chamber along the surface of the door handle along a predetermined path along an axis of the surface of the door handle from a first position to a second position;
the at least one portion of the surface of the door handle contacted by the ultraviolet light changing as a result of the chamber moving from the first position to the second position.

2. The system for disinfecting of claim 1, wherein the ultraviolet light is applied to the surface via a light guide.

3. The system for disinfecting of claim 1, further comprising a dock connectable to the chamber, the dock capable of providing a resource to the chamber.

4. The system for disinfecting of claim 3, further comprising a battery in the chamber, wherein the resource is electricity and the battery is charged by the dock.

5. The system for disinfecting of claim 1, further comprising an actuator for starting the motor to move the chamber from the first position to the second position.

6. The system for disinfecting of claim 5, wherein the actuator is a sensor that detects presence or non-presence of an object.

7. The system for disinfecting of claim 5, wherein the actuator is a sensor that detects touch.

8. The system for disinfecting of claim 5, wherein the actuator is a button or a computer.

9. The system for disinfecting of claim 5, further comprising:
a computer;
a database accessible to the computer for storage and retrieval of scheduling data;
a user computer device in data communication with the computer;
the actuator in data communication with the computer;
the user computer device creating a command and providing the command to the computer with credentials;
the computer verifying credentials and providing the command to the actuator for disinfection.

10. The system for disinfecting of claim 9, the actuator providing a status to the computer upon successful completion of the command.

11. The system for disinfecting of claim 9, wherein the command is to schedule actuation.

12. The system for disinfecting of claim 1, the chamber being closed at opposite ends along the axis of the surface to limit ultraviolet light from leaving the chamber.

13. The system for disinfecting of claim 12, the chamber is closed by at least one gasket.

14. A system for disinfecting, comprising:
a door having a door handle with a surface to be disinfected;
a chamber having an inner housing, the chamber at least partially surrounding the surface to be disinfected;
an ultraviolet lamp located at the inner housing to apply an ultraviolet light to at least one portion of the surface to be disinfected;
a motor for moving the chamber along the surface to be disinfected along a predetermined path along an axis of the surface to be disinfected from a first position to a second position;
the at least one portion of the surface to be disinfected contacted by the ultraviolet light changing as a result of the chamber moving from the first position to the second position;
a computer;
a database accessible to the computer for storage and retrieval of scheduling data;
a user computer device in data communication with the computer; and
an actuator in data communication with the computer;
the user computer device creating a command and providing the command to the computer with credentials;
the computer verifying credentials and providing the command to the actuator for disinfection.

* * * * *